(12) United States Patent
Pines et al.

(10) Patent No.: US 8,410,120 B2
(45) Date of Patent: Apr. 2, 2013

(54) COMPOSITION AND METHOD FOR TREATING OR PREVENTING SKELETAL MUSCLE FIBROSIS

(76) Inventors: Mark Pines, Rehovot (IL); Arnon Nagler, Jerusalem (IL)

( * ) Notice: Subject to any disclaimer, the term of this patent is extended or adjusted under 35 U.S.C. 154(b) by 470 days.

(21) Appl. No.: 12/523,954

(22) PCT Filed: Jan. 21, 2008

(86) PCT No.: PCT/IL2008/000088
§ 371 (c)(1),
(2), (4) Date: Feb. 15, 2010

(87) PCT Pub. No.: WO2008/087650
PCT Pub. Date: Jul. 24, 2008

(65) Prior Publication Data
US 2010/0144766 A1 Jun. 10, 2010

Related U.S. Application Data

(60) Provisional application No. 60/885,896, filed on Jan. 21, 2007.

(51) Int. Cl.
*A61K 31/505* (2006.01)
*A61K 31/517* (2006.01)

(52) U.S. Cl. .............. 514/266.22; 514/266.23; 514/259

(58) Field of Classification Search ............. 514/266.22, 514/266.23, 259
See application file for complete search history.

(56) References Cited

U.S. PATENT DOCUMENTS

| | | | |
|---|---|---|---|
| 3,320,124 | A | 5/1967 | Waletzky |
| 4,824,847 | A | 4/1989 | Raether |
| 4,855,299 | A | 8/1989 | Raether |
| 4,861,758 | A | 8/1989 | Raether |
| 5,215,993 | A | 6/1993 | Schildknecht et al. |
| 5,449,678 | A | 9/1995 | Pines et al. |
| 5,891,879 | A | 4/1999 | Nagler et al. |
| 6,028,075 | A | 2/2000 | Pines et al. |
| 6,090,814 | A | 7/2000 | Nagler et al. |
| 6,211,188 | B1 | 4/2001 | Pines et al. |
| 6,562,829 | B1 | 5/2003 | Pines et al. |

FOREIGN PATENT DOCUMENTS

| | | |
|---|---|---|
| WO | 98/43642 A1 | 10/1998 |
| WO | 00/09070 A2 | 2/2000 |
| WO | 01/17531 A1 | 3/2001 |

(Continued)

OTHER PUBLICATIONS

Pines et al, Gen. Pharmac. vol. 30, No. 4, pp. 445-450, 1998.*

(Continued)

*Primary Examiner* — Savitha Rao
(74) *Attorney, Agent, or Firm* — Lando & Anastasi LLP

(57) ABSTRACT

A compound in combination with a pharmaceutically acceptable carrier, the compound having a formula: wherein: $R_1$ is a member of the group consisting of hydrogen, halogen, nitro, benzo, lower alkyl, phenyl, and lower alkoxy; $R_2$ is a member of the group consisting of hydroxy, acetoxy, and lower alkoxy; and $R_3$ is a member of the group consisting of hydrogen and lower alkenoxy-carbonyl; and n is either 1 or 2; and pharmaceutically acceptable salts thereof; for use in treatment of or prevention of skeletal muscle fibrosis and/or for inducing skeletal muscle regeneration.

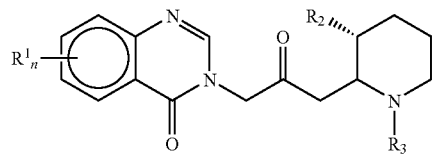

5 Claims, 4 Drawing Sheets

FOREIGN PATENT DOCUMENTS

WO 02/094178 A2 11/2002

OTHER PUBLICATIONS

Xavier et al., The Journal of Biological chemistry, vol. 279, No. 15, 2004, pp. 15167-15176.*

McGaha et al, The Journal of investigative dermatology, vol. 118, No. 3, 2002, pp. 461-470.*

Chen et al., Neurology, vol. 65, 2005, pp. 826-834.*

Barnasconi et al., J. Olin. invest. vol. 96, 1995, pp. 1137-1144).*

Backman et al. "Low-dose prednisolone treatment in Duchenne and Becker muscular dystrophy." Neuromuscul Disord., vol. 5, pp. 233-241, 1995.

Choi et al., "Halofuginone, a specific collagen type I inhibitor, reduces anastomotic intimal hyperplasia" Arch. Surg., vol. 130, pp. 257-261, 1995.

Dubowitz, "Therapeutic possibilities in muscular dystrophy: the hope versus the hype" Neuromuscul Disord., vol. 12, pp. 113-116, 2002.

Dunace, et al. "A role for collagen in the pathogenesis of muscular dystrophy?", Nature, vol. 284, pp. 470-472, 1980.

Emery, "Population frequencies of inherited neuromuscular diseases—a world survey", Neuromusc. Disord. vol. 1, pp. 19-29, 1991.

Fingl, et al., "The Pharmacological Basis of Therapeutics", Ch. 1 p. 1, 1975.

Finsterer, "The Heart in Human Dystrophinopathies", Cardiology, vol. 99, pp. 1-19, 2003.

Granot, et al. "Halofuginone: An inhibitor of collagen type I synthesis", Biochim Biophys Acta, vol. 1156, pp. 107-112, 1993.

Halevy, et al. "Inhibition of muscle fibrosis and improvement of muscle histopathology in dysferlin knock-out mice treated with halofuginone" Histology & Histopathology (in press), (2012).

Hantai et al. "Fibronectin, laminin, type I, III and IV collagens in Duchenne's muscular dystrophy, congenital muscular dystrophies and congenital myopathies: an immunocytochemical study." Connect Tissue Res., vol. 13, pp. 273-281, 1985.

Hoffman, et al. "Dystrophin: the protein product of the Duchenne muscular dystrophy locus", Cell, vol. 51, pp. 919-928, 1987.

Khurana, et al. "Pharmacological strategies for muscular dystrophy", Nat Rev Drug Discov. 2:379-90, 2003.

Krang, et al. "Harnessing the potential of dystrophin-related proteins for ameliorating Duchenne's muscular dystrophy." Acta Physiol Scand. vol. 171, pp. 349-358, 2001.

Langley, et al. "Myostatin inhibits myoblast differentiation by down-regulating MyoD expression.", J Biol Chem., vol. 277, pp. 49831-49840, 2002.

Law, et al. "Human gene therapy with myoblast transfer" Transplant Proc. 29(4):2234-7, 1997.

Levi-Schaffer, et al. "Inhibition of collagen synthesis and changes in skin morphology in murine graft-versus-host disease and tight skin mice: effect of halofuginone" J Invest Dermatol, vol. 106, pp. 84-88, 1996.

Lu, et al. "Functional amounts of dystrophin produced by skipping the mutated exon in the mdx dystrophic mouse" Nat. Med. vol. 9(8), pp. 1009-1014, 2003.

Michele et al. "Dystrophin-glycoprotein complex: post-translational processing and dystroglycan function" J. Biol. Chem. vol. 278, pp. 15457-15460, 2003.

Nevo, et al., "Fibrosis Inhibition and Muscle Histopathology Improvement in Laminin-a2-Deficient Mice" Muscle & Nerve Aug. 2010.

Pines et al. "Halofuginone: From Veterinary Use to Human Therapy" Drug Develop. Res. 50, 371-378 (2000).

Prockop, "Collagens: molecular biology, diseases, and potentials for therapy" Annu Rev Biochem. vol. 64, pp. 403-434, 1995.

Rafael, et al., "Venezuelan hemorrhagic fever: eight years of observation" Acta Cient Venez., vol. 49 Suppl 1, pp. 46-51, 1997. (Article in Spanish, English abstract attached).

Skuk, et al. "Experimental and therapeutic approaches to muscular dystrophies." Curro Opin. Neurol. vol. 15, pp. 563-569, 2002.

Thiodellet, et al. "Current protocol of a research phase I clinical trial of full-length dystrophin plasmid DNA in Duchenne/Becker muscular dystrophies" Neuromuscul Disord., vol. 12 Suppl 1, pp. S49-S51, 2002.

Turgeman, et al., "Prevention of muscle fibrosis and improvement in muscle performance in the mdx mouse by halofuginone" Neuromuscular Disorders 18 (2008) 857-868.

Wanger, et al. "Loss of myostatin attenuates severity of muscular dystrophy in mdx mice" Ann Neurol. vol. 52, pp. 832-836, 2002.

Wells, et al. "Gene transfer studies in animals: what do they really tell us about the prospects for gene therapy in DMD? " Neuromuscle Disord.vol. 12 Suppl, pp. S11-S22, 2002.

Yue, et al. "Microdystrophin gene therapy of cardiomyopathy restores dystrophin-glycoprotein complex and improves sarcolemma integrity in the mdx mouse heart" Circulation, vol. 108, pp. 1626-1632, 2003.

Zhang, et al. "Synergistic cooperation between Sp1 and Smad3/Smad4 mediates transforming growth factor beta1 stimulation of alpha 2(I)-collagen (COL1A2) transcription." J. Biol. Chem. vol. 275, pp. 39237-39245, 2000.

Zhao, et al. "Platelet-derived growth factor and its receptors are related to the progression of human muscular dystrophy: an immunohistochemical study." J. Patho. vol. 201, pp. 149-159, 2003.

Zhu, et al. "Myostatin signaling through Smad2, Smad3 and Smad4 is regulated by the inhibitory Smad7 by a negative feedback mechanism" Cytokine., vol. 26(6), pp. 262-272; Fig. 1, 2004.

* cited by examiner

COMPOSITION AND METHOD FOR TREATING OR PREVENTING SKELETAL MUSCLE FIBROSIS

CROSS-REFERENCE TO RELATED APPLICATIONS

This application is a U.S. National Phase Application under 35 U.S.C. 371 of PCT International Application No. PCT/IL2008/000088, which has an international filing date of Jan. 21, 2008, and which claims priority from U.S. Provisional Patent Application No. 60/885,896, filed on Jan. 21, 2007, which is incorporated herein by reference in its entirety.

FIELD OF THE INVENTION

The present invention relates to a method of treating fibrosis, and more particularly to treatment, prevention or amelioration of skeletal muscle fibrosis by use of halofuginone or related compounds.

BACKGROUND OF THE INVENTION

Muscle fibrosis is a phenomenon that frequently occurs in diseased or damaged muscle. It is characterized by the excessive growth of fibrous tissue, which usually results from the body's attempt to recover from injury. Fibrosis impairs muscle function and causes weakness. The amount of muscle function loss generally increases with the extent of fibrosis. Fibrosis is usually progressive and can contribute to the patient's inability to carry out ordinary tasks of independent living, such as grasping objects or walking. Fibrosis commonly occurs as a result of muscular dystrophy, as well as due to other afflictions, such as denervation atrophy, a degradation of muscle tissue caused by loss of neural contact to a muscle. For some types of muscular dystrophy, such as Duchenne, fibrosis can result in death as the muscles of the diaphragm are affected (the diaphragm is a skeletal muscle which is involuntary rather than voluntary).

Muscular dystrophies are a heterogeneous group of genetic disorders characterized by the progressive loss of muscle strength and integrity. Dystrophic muscle shows variation in muscle fiber size, infiltration of connective and fatty tissue, and centrally located nuclei. The membranes of the fibers are fragile and extensive damage occurs, leading to necrosis and muscle wasting.

Victims of muscular dystrophies, particularly Becker muscular dystrophy (BMD) and Duchenne muscular dystrophy (DMD), frequently suffer from increasing skeletal muscle fibrosis as the disease progresses.

The most common form of muscle dystrophy is the X-linked recessive DMD, a severely penetrating allelic manifestation which affects 1 in 3500 live males at birth; about a third of cases occur as de novo mutations in the infant (Emery A E. (1991) Neuromusc. Disord. 1:19-29).

Usually the disease is diagnosed at 4-5 years of age and by 8-10 years, deterioration of the patient's condition necessitates wheelchair use. By their early teens, further neurological and cardiological symptoms are apparent. Progression of muscle degeneration and worsening clinical symptoms, lead to death in the late teens or early twenties, typically as a result of cardio-pulmonary complications due to fibrosis of the diaphragm.

The leading causes of death in DMD victims, respiratory and heart failure, result from weakness in diaphragm and myocardium muscles that are most affected by fibrosis (Finsterer, (2003) Cardiology 99:1-19). Fibrosis is characterised by an increase in extra-cellular matrix (ECM) constituents especially collagen type I. Both in DMD and Congenital muscular dystrophy (CMD), an increase in type I and III collagens were observed in the skeletal muscle (Hantai et al. (1985) Connect Tissue Res. 13:273-81 and Dunace, et al. (1980) Nature 284:470-472) leading to fibrosis, which correlated with muscle destruction (Zhao, et al. (2003) J. Patho. 201:149-59). The cardiac involvement in DMD is characterized pathologically by degeneration and fibrosis of the myocardium, probably due to myofibroblast activity, centering around the posterolateral wall of the left ventricle.

BMD is a less severe condition than DMD, characterized by slowly progressive muscle weakness of the legs and pelvis, again due to fibrosis of the muscles (although for BMD the skeletal muscles are more greatly affected). The advance of fibrosis often causes ever greater loss of mobility and a reduced life expectancy. At some point, the patient may become too weak to walk and takes to a wheelchair.

Both BMD and DMD are associated with defects in the dystrophin gene, the gene responsible for the production of dystrophin protein, which is a vital part of the dystrophin-glycoprotein complex. DMD is characterized by the near absence of dystrophin protein in skeletal muscles, while BMD results from different mutations in the same gene, resulting in decreased or damaged dystrophin. The presence of some dystrophin protects the muscles of those with BMD from degenerating as badly or as quickly as those of DMD victims.

The dystrophin-glycoprotein complex connects the actin cytoskeleton of myofibres to the extracellular matrix (ECM) and is therefore integral to the contractile structure of muscle (Yue Y, et al. (2003) Circulation, 108:1626-32 and Michele et al. (2003) J. Biol. Chem. 278:15457-60). The preliminary stage of DMD is characterized by the presence of focal groups of necrotic myofibres, muscle hypertrophy and abnormally high levels of muscle creatine kinase (CK). In the pathological phase, repeated cycles of degeneration exhaust the regenerative capacity of muscle-specific progenitor cells (satellite cells) and fibrotic mechanisms cause the progressive replacement of the muscle tissue with collagenous connective tissue (Rafael et al., 1997). These processes lead to joint contraction, loss of ambulation and death from respiratory or cardiac failure (Wells, et al. (2002) Neuromuscle Disord. 12 Suppl 1:S11-22).

The perfect solution for DMD and BMD patients would be to place a normal copy of the dystrophin gene into muscle cells, and hence restore sufficient protein expression to improve structure and function (Khurana, et al. (2003) Nat Rev Drug Discov. 2:379-90). At 3.0 MB the dystrophin gene is vast, and successful therapy would require massive and sustained gene transfer (Hffman, et al. (1987) Cell 51:919-28 and Skuk, et al. (2002) Curr. Opin. Neurol. 15:563-9 and Thioudellet, et al. (2002) Neuromuscul Disord. 12 Suppl 1:S49-51). Muscle fibrosis is a major obstacle in gene therapy since it hampers gene delivery.

An alternative to replacing the faulty gene is to modulate its expression by employing antisense oligonucleotides that alter RNA stability, or splicing (Lu Ql, et al. (2003) Nat. Med. 9(8):1009-14 and Rando T A. (2002) Am. J. Phy. Med. Rehabil. 81(11Suppl):S175-86), thereby resulting in the production of a functional protein. Transplantation of muscle precursor cells (myoblast transfer) has also been explored as a method for restoring dystrophin protein to dystrophic muscle (Law P K et al. (1997) Transplant Proc. 29(4):2234-7). This technique is constrained by the difficulties associated with treating large volumes of muscle with long-lasting effect. An alternative approach is to up-regulate the expression of an endogenous protein that effects some functional replacement (Krag T O, et al. (2001) Acta Physiol Scand. 171:349-58). However, all of these treatments are ineffective unless the progression of the underlying fibrotic condition can be halted or at least ameliorated somewhat.

The crucial role of collagen in fibrosis has prompted attempts to develop agents that inhibit or modulate its accumulation. Several unique post-transcriptional enzymes of the collagen biosynthesis pathway appear to be attractive targets for reducing the formation of collagen fibers or for the accumulation of fibers with altered properties (Prockop D J, (1995) Annu Rev Biochem. 64:403-34).

The major disadvantage of these inhibitors is that they are not collagen-type-specific and may inhibit the biosynthesis of other collagens with serious toxic consequences.

To date there is no effective therapy for reducing skeletal muscle fibrosis. No treatment which affects fibrotic tissue without adversely affecting healthy muscle tissue or other body functions is currently known. The only treatment to have shown clinical efficacy is a prednisone/prednisolone treatment that results in a modest increase in strength, and delays, but does not halt, the progress of the disease (Backman, et al. Neuromuscul Disord. 5:233-41 and Dubowitz, (2002) Neuromuscul Disord. 12:113-6).

There is thus a widely recognized need for, and it would be highly advantageous to have, a method of preventing or retarding the build up of skeletal muscle fibrosis that accompanies disorders such as Duchenne and Becker muscular dystrophies and other muscle dystrophies with extensive fibrosis, as well as to reduce the effect on muscles of the diaphragm for Duchenne muscular dystrophy.

Quinazolinone Derivatives

Quinazolinone derivatives were first taught in U.S. Pat. No. 3,320,124 to American Cyanamid as a treatment for the intestinal parasitic disease, coccidiosis. Halofuginone, (7-bromo-6-chloro-3-[3-(3-hydroxy-2-piperidinyl)-2-oxopropyl]-4 (3H)-quinazolinone), an analog of a plant alkaloid originally isolated from the plant *Dichroa febrifuga*, was described as the preferred quinazolinone derivative. Subsequently, U.S. Pat. Nos. 4,824,847; 4,855,299; 4,861,758 and 5,215,993 all relate to the coccidiocidal properties of halofuginone.

More recently, it was disclosed in U.S. Pat. No. 5,449,678 that these quinazolinone derivatives are unexpectedly useful for the treatment of a fibrotic condition such as scleroderma and graft-versus-host disease (GVHD). This disclosure provided compositions of a specific inhibitor comprising a therapeutically effective amount of a pharmaceutically active compound of the formula:

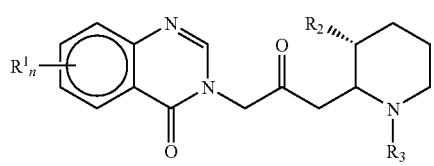

(I)

wherein: n=1-2
$R_1$ is a member of the group consisting of hydrogen, halogen, nitro, benzo, lower alkyl, phenyl and lower alkoxy;
$R_2$ is a member of the group consisting of hydroxy, acetoxy and lower alkoxy; and
$R_3$ is a member of the group consisting of hydrogen and lower alkenoxy-carbonyl.

Pharmaceutically acceptable salts thereof are also included. Of this group of compounds, halofuginone has been found to be particularly effective for the disclosed treatment.

The clinical potential of halofuginone in anti-fibrotic therapy has also been described in Pines, et al. Drug of the Future 21:569-599 and Pines, et al. (1997) Gen. Pharmaco. 30:445-450 and Pines, et al. (2000) Drug Develop. Res. 50, 371-378). Halofuginone, an inhibitor of collagen type I synthesis has been found to inhibit the gene expression of collagen type I, but not of type II (Granot, et al. Biochim Biophys Acta 1156:107-112) or type III (Choi, et al. (1995) Arch Surg 130:257-261).

U.S. Pat. No. 5,891,879 further discloses that the quinazolinone derivatives are effective in treating restenosis. The two earlier-described conditions, scleroderma and graft-versus-host disease, are associated with excessive collagen deposition, which can be inhibited by halofuginone. Restenosis is characterized by smooth muscle cell proliferation and extracellular matrix accumulation within the lumen of affected blood vessels in response to a vascular injury (Choi et al., Arch. Surg., 130:257-261 (1995)). One hallmark of such smooth muscle cell proliferation is a phenotypic alteration, from the normal contractile phenotype to a synthetic one. Type I collagen has been shown to support such a phenotypic alteration, which can be blocked by halofuginone (Choi et al., Arch. Surg., 130: 257-261, (1995); U.S. Pat. No. 5,449,678).

Notably, the in vitro action of halofuginone does not always predict its in vivo effects. For example, as demonstrated in U.S. Pat. No. 5,449,678, halofuginone inhibits the synthesis of collagen type I in bone chrondrocytes in vitro. However, chickens treated with halofuginone were not reported to have an increased rate of bone breakage, indicating that the effect is not seen in vivo. In addition, even though halofuginone inhibits collagen synthesis by fibroblasts in vitro, it promotes wound healing in vivo (WO 01/17531). Thus, the exact behavior of halofuginone in vivo cannot always be accurately predicted from in vitro studies.

Quinazolinone-containing pharmaceutical compositions, including halofuginone, have been disclosed and claimed as effective for treating malignancies (U.S. Pat. No. 6,028,075), for prevention of neovascularization (U.S. Pat. No. 6,090, 814), as well as for treating hepatic fibrosis (U.S. Pat. No. 6,562,829), pulmonary fibrosis (WO 98/43642) and renal fibrosis (WO 02/094178), scleroderma and a variety of other serious diseases, exhibit excessive production of connective tissue, which results in the destruction of normal tissue architecture and function.

WO 00/09070 relates to a method for treating and preventing fibrotic process, which results from pathophysiological responses to tissue trauma, preferably cardiac fibrosis.

In most animal models of fibrosis, regardless of the tissue, halofuginone has a minimal effect on collagen content in the non-fibrotic animals, whereas it exhibits a profound inhibitory effect in the fibrotic organs. This suggests a different regulation of the low level house-keeping expression of collagen type I genes on the one hand and the over-expression induced by the fibrogenic stimulus which is usually an aggressive and a rapid process, on the other.

Muscle Tissue

Muscle is a very specialized tissue that has both the ability to contract and the ability to conduct electrical impulses. Muscles are classified both functionally as either voluntary or involuntary, and structurally as either striated or smooth. From this, there emerge three types of muscles: smooth muscle (involuntary), skeletal voluntary muscle (voluntary and involuntary) and cardiac muscle. Skeletal and cardiac muscle are called striated muscle because of their striped appearance under a microscope.

Skeletal muscle may be of the voluntary or involuntary muscle type, being innervated by neurons that originate from the somatic or voluntary branch of the nervous system, providing willful control of the skeletal muscles, or, as in the case of the diaphragm muscles, being controlled by efferent nerves from the respiratory centre which pass down the spinal cord to the diaphragm.

Skeletal muscle cells are long multi-nucleated cylinders, which acquired this characteristic because they develop from the fusion of small single cells into long units. The cells may vary in diameter, averaging between 100 and 150 microns. Skeletal muscle cells are independent cells separated from one another by connective tissue and must each be stimulated by axons of a neuron. All the cells innervated by branches from the same neuron will contract at the same time and are referred to as a motor unit. Motor units vary in size: large motor units with more than 100 cells are typical of the slow acting postural muscles. Very small motor units with around 10 cells or so are typical of fast acting muscles with very precise control such as those which move the eye. Most human muscles have a mixture of motor units of different sizes.

Skeletal muscles have distinct stripes or striations that identify them and are related to the organization of protein myofilaments inside the cell. Skeletal muscle cells are associated with a type of stem cell known as a satellite cell. These cells are believed to aid in recovery of muscle fibers from damage and can contribute their nuclei to replace and supplement the nuclei of the damaged cells. This occurs in response to the "microtears" produced by strenuous exercise and results in increased production of proteins and myofibrils.

Voluntary muscles comprise a variety of fiber types which are specialized for particular tasks. Most voluntary muscles contain a mixture of fiber types although one type may predominate.

Type 1 or slow oxidative fibers have a slow contraction speed and a low myosin ATPase activity. These cells are specialized for steady, continuous activity and are highly resistant to fatigue. Their motor neurons are often active, with a low firing frequency. These cells are thin (high surface to volume ratio) with a good capillary supply for efficient gas exchange. They are rich in mitochondria and myoglobin, which gives them a red color. They are built for aerobic metabolism and prefer to use fat as a source of energy. These are the marathon runner's muscle fibers.

Type 2A or fast oxidative-glycolytic fibers have a fast contraction speed and a high myosin ATPase activity. They are progressively recruited when additional effort is required, but are still very resistant to fatigue. Their motor neurons show bursts of intermittent activity. These cells are thin (high surface to volume ratio) with a good capillary supply for efficient gas exchange. They are rich in mitochondria and myoglobin which gives them a red color. They are built for aerobic metabolism and can use either glucose or fats as a source of energy. These are general purpose muscle fibers which give the edge in athletic performance, but they are more expensive to operate than type 1.

Type 2B or fast glycolytic fibers have a fast contraction speed and a high myosin ATPase activity. They are only recruited for brief maximal efforts and are easily fatigued. Their motor neurons transmit occasional bursts of very high frequency impulses. These are large cells with a poor surface to volume ratio and their limited capillary supply slows the delivery of oxygen and removal of waste products. They have few mitochondria and little myoglobin, resulting in a white color (e.g. chicken breast). They generate ATP by the anaerobic fermentation of glucose to lactic acid. These are sprinter's muscle fibers, no use for sustained performance.

Cardiac muscle is the muscle found in the heart. It is composed of much shorter cells than skeletal muscle that branch to connect to one another. These connections are by means of gap junctions called intercalated disks that allow an electrochemical impulse to pass to all the connected cells. This causes the cells to form a functional network called a syncytium in which the cells work as a unit. Many cardiac muscle cells are myogenic which means that the impulse arises from the muscle, not from the nervous system. This causes the heart muscle and the heart itself to beat with its own natural rhythm. But the autonomic nervous system controls the rate of the heart and allows it to respond to stress and other demands. As such the heart is said to be involuntary.

The cardiac muscle has a number of unique features that reflect its function of pumping blood.

The myofibrils of each cell (and cardiac muscle is made of single cells—each with a single nucleus) are branched.

The branches interlock with those of adjacent fibers by adherens junctions. These strong junctions enable the heart to contract forcefully without ripping the fibers apart.

The action potential that triggers the heartbeat is generated within the heart itself. Motor nerves (of the autonomic nervous system) do run to the heart, but their effect is simply to modulate—increase or decrease—the intrinsic rate and the strength of the heartbeat. Even if the nerves are destroyed (as they are in a transplanted heart), the heart continues to beat.

The action potential that drives contraction of the heart passes from fiber to fiber through gap junctions.

Due to the numerous structural and functional differences between various muscle types, the effect of an active pharmaceutical ingredient on a particular muscle type cannot be predicted with any degree of reliability according to the effect of that ingredient on a different muscle type.

SUMMARY OF THE INVENTION

The present invention successfully addresses the shortcomings of the presently known methods of treating and/or preventing skeletal muscle fibrosis by providing compositions and methods comprising a quinizolinone derivative.

As used herein, the quinazolinone derivative comprises a compound having a formula:

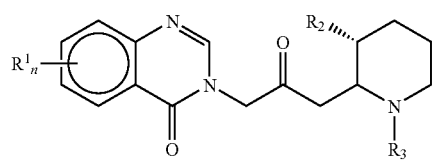

wherein:
$R_1$ is a member of the group consisting of hydrogen, halogen, nitro, benzo, lower alkyl, phenyl, and lower alkoxy; $R_2$ is a member of the group consisting of hydroxy, acetoxy, and lower alkoxy; and $R_3$ is a member of the group consisting of hydrogen and lower alkenoxy-carbonyl; and n is either 1 or 2; and pharmaceutically acceptable salts thereof.

According to one aspect of the present invention there is provided a pharmaceutical composition for treating and/or preventing and/or at least reducing the rate of progression of skeletal muscle fibrosis in a subject in need thereof, the composition comprising a pharmaceutically effective amount of a quinizolinone derivative and pharmaceutically acceptable salts thereof; and a pharmaceutically acceptable carrier.

According to another aspect of the present invention there is provided a pharmaceutical composition for improving skeletal muscle regeneration in a subject in need thereof, the composition comprising a pharmaceutically effective amount of a quinazolinone derivative and pharmaceutically acceptable salts thereof; and a pharmaceutically acceptable carrier.

According to yet another aspect of the present invention there is provided a method for reducing the progression of skeletal muscle fibrosis in a subject in need thereof, the method comprising administering a pharmaceutically effective amount of a quinazolinone derivative and pharmaceutically acceptable salts thereof; and a pharmaceutically acceptable carrier.

According to still another aspect of the present invention there is provided a method for improving and/or inducing skeletal muscle regeneration in a subject in need thereof, the method comprising administering a pharmaceutically effective amount of a quinazolinone derivative, and pharmaceutically acceptable salts thereof; and a pharmaceutically acceptable carrier. The improving of skeletal muscle regeneration optionally occurs through inhibiting the TGFβ pathway and/or by inhibiting the Myostatin Smad3-dependent pathway.

According to an additional aspect of the present invention there is provided the use of a quinazolinone derivative, and pharmaceutically acceptable salts thereof; in the manufacture of a medicament for reducing the progression of skeletal muscle fibrosis in a subject in need thereof.

According to further features in preferred embodiments of the invention described below, quinazolinone derivative is optionally and preferably halofuginone.

According to still further features in the described preferred embodiments, the subject in need of treatment by the compositions and methods of the present invention is suffering from a disorder which targets skeletal muscle tissue, such as, for example muscular dystrophy, including Duchenne muscular dystrophy, Becker muscular dystrophy, Emery-Dreifuss Muscular Dystrophy, Limb-Girdle Muscular Dystrophy, Facioscapulohumeral Muscular Dystrophy, Myotonic Dystrophy, Oculopharyngeal Muscular Dystrophy, Distal Muscular Dystrophy, and congenital muscular dystrophy.

Alternatively, the subject may be suffering from denervation atrophy.

Optionally, the skeletal muscle tissue targeted by the disorder may comprise diaphragm muscle.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

The term "comprising" means that other steps and ingredients that do not affect the final result can be added. This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

The term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The term "active ingredient" refers to a pharmaceutical agent including any natural or synthetic chemical substance that subsequent to its application has, at the very least, at least one desired pharmaceutical or therapeutic effect.

The term "therapeutically effective amount" or "pharmaceutically effective amount" denotes that dose of an active ingredient or a composition comprising the active ingredient that will provide the therapeutic effect for which the active ingredient is indicated.

As used herein, the term "pharmaceutically acceptable" means approved by a regulatory agency of the Federal or a state government or listed in the U.S. Pharmacopeia or other generally recognized pharmacopeia for use in animals, and more particularly in humans. Herein, the phrases "physiologically suitable carrier" and "pharmaceutically acceptable carrier" are interchangeably used and refer to an approved carrier or a diluent that does not cause significant irritation to an organism and does not abrogate the biological activity and properties of the administered conjugate.

As used herein, the term "carrier" refers to a diluent, adjuvant, excipient, or vehicle with which the therapeutic is administered.

Herein the term "excipient" refers to an inert substance added to a pharmaceutical composition to further facilitate processes and administration of the active ingredients.

As used herein, the singular form "a," "an," and "the" include plural references unless the context clearly dictates otherwise. For example, the term "a compound" or "at least one compound" may include a plurality of compounds, including mixtures thereof.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

The present invention is of a method and pharmaceutical composition for treating or preventing skeletal muscle fibrosis in a subject, or at least reducing the progression thereof, by using a quinazolinone derivative, preferably halofuginone. According to preferred embodiments, the present invention relates to a method and pharmaceutical compositions for at least reducing the progressive loss of muscle strength and/or function associated with skeletal muscle fibrosis in a subject. Optionally and preferably, such at least reduction of the progressive loss of muscle strength and/or function and/or treatment and/or prevention occurs in a subject suffering from skeletal muscle fibrosis associated with a disease of which directly or indirectly causes such fibrosis, including but not limited to muscular dystrophy or denervation atrophy. Muscular dystrophy includes Duchenne Muscular Dystrophy; Becker Muscular Dystrophy; Emery-Dreifuss Muscular Dystrophy; Limb-Girdle Muscular Dystrophy; Facioscapulohumeral Muscular Dystrophy (also known as Landouzy-Dejerine); Myotonic Dystrophy; Oculopharyngeal Muscular Dystrophy; Distal Muscular Dystrophy; and Congenital Muscular Dystrophy.

Unexpectedly, according to preferred embodiments of the present invention, a quinazolinone derivative, preferably halofuginone, may optionally and preferably be used to at least delay the progression of fibrosis of the diaphragm in a subject suffering from a disease which affects this involuntary muscle, including but not limited to Duchenne muscular dystrophy. More preferably, the present invention relates to treating and/or preventing fibrosis of the diaphragm in a subject suffering from such a disease.

According to preferred embodiments of the present invention and as demonstrated below, one or more types of muscle cells may optionally and preferably be able to regenerate themselves as a result of administration of a quinazolinone derivative, preferably halofuginone, to a subject in need thereof.

The principles and operation of the compositions and methods according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Figure 1:
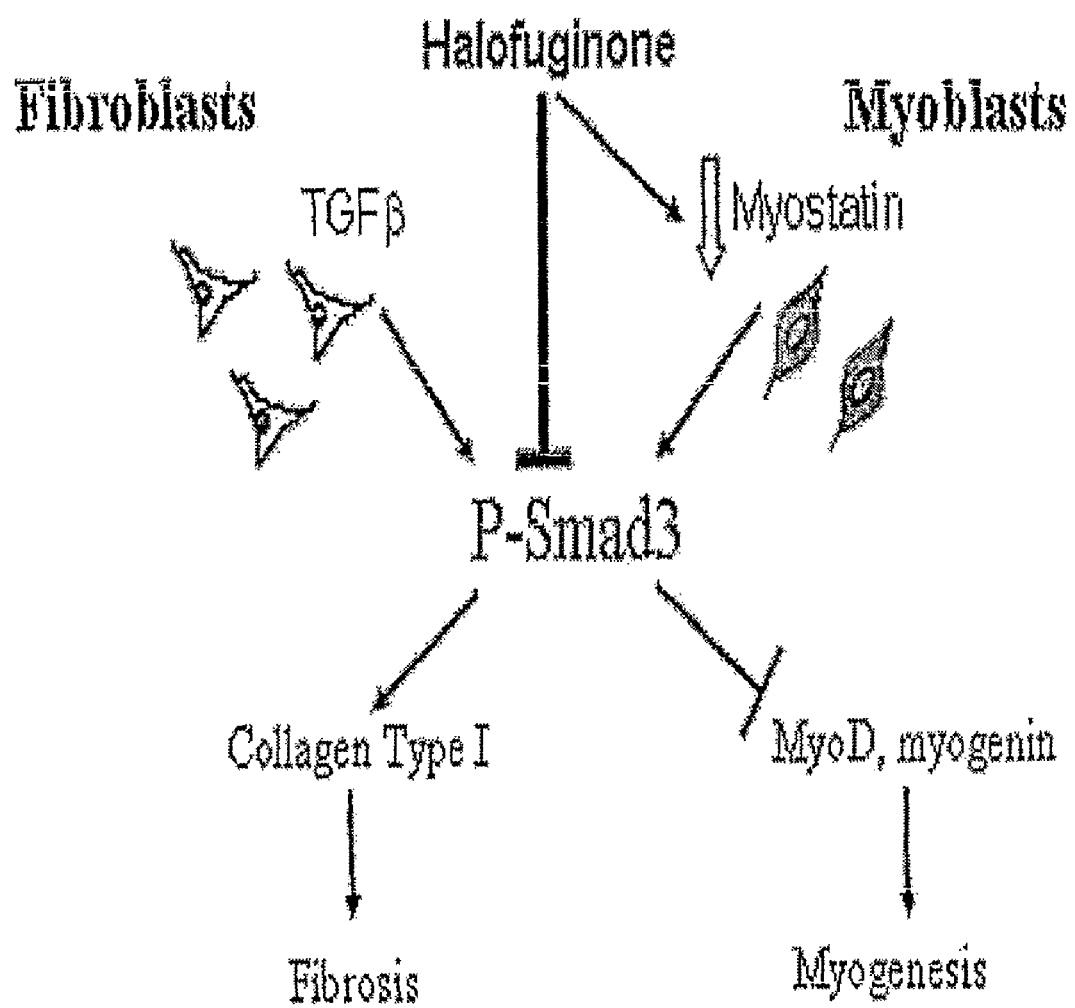
FIG. 1 shows the effect of halofuginone on fibrosis and myogenesis via Smad3-dependent pathways.

Myostatin is a transforming growth factor-β (TGF-β) family member that plays an essential role in regulating skeletal muscle growth, by inhibition of the proliferation and differentiation of myeloblasts, via inhibition of muscle-specific MyoD and myogenin genes. Signaling occurs via activation of Smad3 proteins (Langley, et al. (2002) J Biol. Chem. 277:49831-40 and Zhang, et al. (2000) J. Biol. Chem. 275: 39237-45 and Zhu, et al. (2004) Cytokine. 26(6):262-72; FIG. 1).

TGFβ is the major stimulator of collagen synthesis, particularly collagen type I, in fibroblasts leading to fibrosis. The inverse correlation between fibrosis and muscle formation in dystrophy has been demonstrated (Wanger, et al. (2002) Ann Neurol. 52:832-6).

It has been demonstrated that halofuginone, an inhibitor of Smad3 activity (McGaha, et al. (2002) J Invest Dermatol. 118(3):461-70), is a potent inhibitor of fibrosis due to its effect on collagen biosynthesis and degradation in variety of tissues (Levi-Schaffer, et al. (1996) J Invest Dermatol 106: 84-88). The tissue types studied did not include skeletal muscle. Furthermore, the prior art does not teach the use of halofuginone in regeneration of muscle.

Preliminary experiments by the present inventors have demonstrated a halofuginone-dependent inhibition in myostatin gene expression in fibrotic liver. Halofuginone is to date the only known collagen type-specific inhibitor on the transcriptional level. Inhibition of collagen synthesis on the transcriptional level is more effective than attempting to treat the consequences of collagen overproduction, which is the aim of other antifibrotic drugs.

Due to the numerous structural and functional differences between various muscle types, the effect of an active pharmaceutical ingredient on a particular muscle type cannot be predicted with any degree of reliability.

Therefore, it was hypothesized that halofuginone may improve skeletal muscle integrity and inhibit fibrosis in a subject, as a consequence of its combined effect on inhibition of collagen type I synthesis, increase in collagen degradation and improved muscle regeneration by inhibiting TGFβ and myostatin Smad3-dependent pathways, as shown in FIG. 1. Also, halofuginone may inhibit myostatin gene expression in muscle as well as was shown in other tissues causing a further increase in muscle regeneration.

Hereinafter, the term "halofuginone" is defined as a compound having the formula:

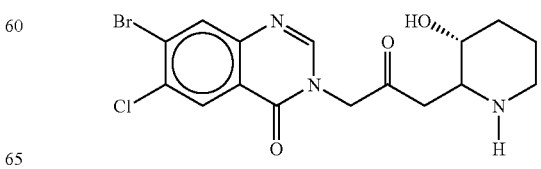

and pharmaceutically acceptable salts thereof.

The phrase "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound.

Although the specific quinazolinone derivative "halofuginone" is referred to throughout the specification, it is understood that other quinazolinone derivatives may be used in its place, these derivatives having the general formula:

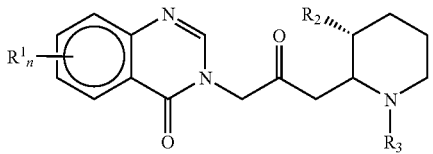

wherein: n=1-2
$R_1$ is a member of the group consisting of hydrogen, halogen, nitro, benzo, lower alkyl, phenyl and lower alkoxy;
$R_2$ is a member of the group consisting of hydroxy, acetoxy and lower alkoxy; and
$R_3$ is a member of the group consisting of hydrogen and lower alkenoxy-carbonyl,
and pharmaceutically acceptable salts thereof.

The terms "skeletal muscle fibrosis" "muscle fibrosis" and "fibrosis" as used herein refer to a phenomenon that frequently occurs in diseased or damaged muscle, characterized by the excessive growth of fibrous tissue, and impairment of muscle function.

Hereinafter, the term "a subject" refers to a human or animal to whom halofuginone was administered.

The term "reducing the extent of" includes both substantially preventing the process of skeletal muscle fibrosis from starting and slowing or halting the progression of skeletal muscle fibrosis once it has arisen.

Compounds which are intended for the inhibition of skeletal muscle fibrosis were tested by an in vivo model for their ability to slow or halt the pathological process leading to deposition of fibrotic tissue. Such experiments were conducted for the collagen type I synthesis inhibitor halofuginone, as described in greater detail in the Examples section below.

The mdx mouse was selected as a model to evaluate the efficacy of halofuginone in prevention and treatment of dystrophy by inhibiting muscle fibrosis (by decreasing collagen synthesis and increasing collagen degradation) and delaying muscle degeneration, and in improving muscle regeneration by inhibiting myostatin signaling.

As shown in the Examples section below, halofuginone was shown to be highly effective in reducing the extent of skeletal muscle fibrosis, and in improving skeletal muscle regeneration, in both skeletal muscle and in muscles of the diaphragm.

The present invention therefore provides a pharmaceutical composition comprising a quinazolinone derivative, such as halofuginone, for reducing the extent of skeletal muscle fibrosis and for improving skeletal muscle regeneration.

The pharmaceutical composition of the present invention comprises, in addition to the quinazolinone derivative, a pharmaceutically acceptable carrier, and may optionally further comprise one or more pharmaceutically acceptable excipients, such as, for example, binding agents, stabilizers, diluents, surfactants, flavors, and odorants.

Pharmaceutically acceptable carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes. Further techniques for formulation and administration of active ingredients may be found in "Remington's Pharmaceutical Sciences," Mack Publishing Co., Easton, Pa., latest edition, which is incorporated herein by reference as if fully set forth herein. Pharmaceutical compositions for use in accordance with the present invention thus may be formulated in conventional manner using one or more pharmaceutically acceptable carriers comprising excipients and auxiliaries, which facilitate processing of the active ingredients into preparations which, can be used pharmaceutically. Proper formulation is dependent upon the route of administration chosen.

The pharmaceutical composition of the present invention may be administered by any route selected from the oral, parenteral, transdermal, intravenous, subcutaneous, intramuscular, intranasal, intraauricular, sublingual, rectal, transmucosal, intestinal, intraauricular, buccal, intramedullar, intrathecal, direct intraventricular, intraperitoneal, or intraocular routes. Preferably, administration is by the oral or parenteral routes.

Hereinafter, the term "oral administration" includes, but is not limited to, administration by mouth for absorption through the gastrointestinal tract, buccal administration and sublingual administration.

For oral administration, the active ingredients can be formulated readily by combining the active ingredients with pharmaceutically acceptable carriers well known in the art. Such carriers enable the active ingredients of the invention to be formulated as tablets, pills, dragees, capsules, liquids, gels, syrups, slurries, powders or granules, suspensions or solutions in water or non-aqueous media, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients such as thickeners, diluents, flavorings, dispersing aids, emulsifiers, binders or preservatives may be desirable.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active ingredient doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

The term "parenteral administration" includes, but is not limited to, administration by intravenous drip or bolus injection, subcutaneous, or intra muscular injection. Formulations for parenteral administration may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

Collagen Content and Collagen α1(I) Gene Expression (in the Quadriceps and Tibialis Muscles Mdx mice were treated either with halofuginone by I.P. injection every other day (3 μg/mouse) starting at 5 weeks of age for 4 weeks, or with saline vehicle. C57B mice were used as controls.

At the end of the 4 week period, tibialis anterior (fast) and quadriceps (slow) muscles were removed for evaluation of fibrosis by Sirius red staining for collagen content, and by in situ hybridization of collagen α1(I) gene expression.

Example 2

Effect of Halofuginone on Fibrosis in the Diaphragm, Gastrochnemius and Tibialis Muscles Halofuginone was administered by I.P injection to mdx mice (n=7) from 3 weeks of age every other day at a concentration of 5 μg/mouse. The wild type (C57/BL) and mdx mice without halofuginone served as controls. At the age of 7 and 11 weeks the mice were sacrificed and the diaphragm, gastrochnemius and the tibialis were fixed for histology and samples were frozen for further analysis. Sections were stained for collagen by Sirius red and with methyl green as a counter stain. Image analysis using the Image Pro software was performed for statistical evaluation of the effect of halofuginone on collagen content. For the image analysis, images were taken from 3 animals/group and 4 replicates from each animal/tissue. The results are the ratio of red (R) to green color (G).

Example 3

Effect of Halofuginone on Muscle Regeneration

Figure 2:
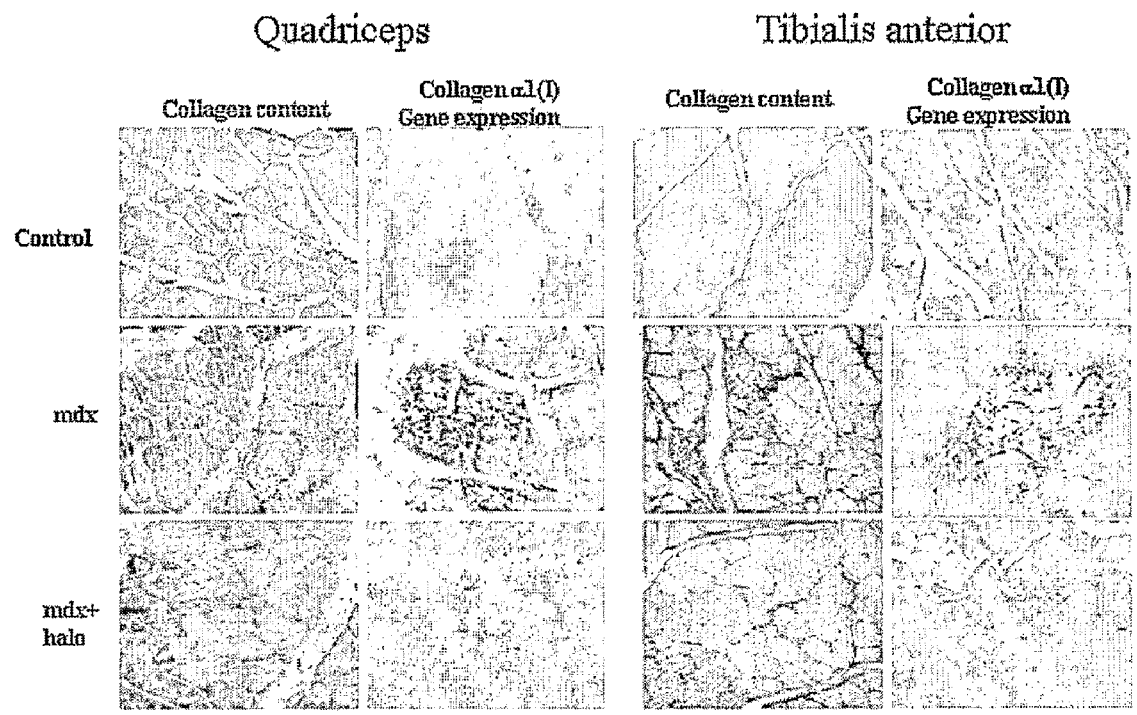
FIG. 2 presents the results of Sirius red staining for collagen content and in situ hybridization of collagen α1(I) gene expression in Mdx mice and C57B control mice, in the presence and absence of halofuginone.

Mdx mice were treated with halofuginone 5 μg or 7.5 μg for 1 or 2 months starting at age of 3 weeks. The untreated mdx mice served as controls. At the end of the experiment, the diaphragms were taken for hematoxyline & eosin staining before central nuclei counting. The results are the mean±SE of 20 photos taken from 3 different mice. Each photo contained approximately 120 fibers Results As shown in FIG. 2, the quadriceps (slow) and tibialis (fast) muscles of the C57B controls showed almost no cells expressing the collagen α1(I) gene, and low levels of collagen surrounding the fibers were observed. A significant increase was observed both in the expression of collagen α1(I) gene and in the amount of collagen fibers in the mdx quadriceps and tibialis muscles compared to the controls. This increase was almost completely prevented by halofuginone treatment.

Figure 3:
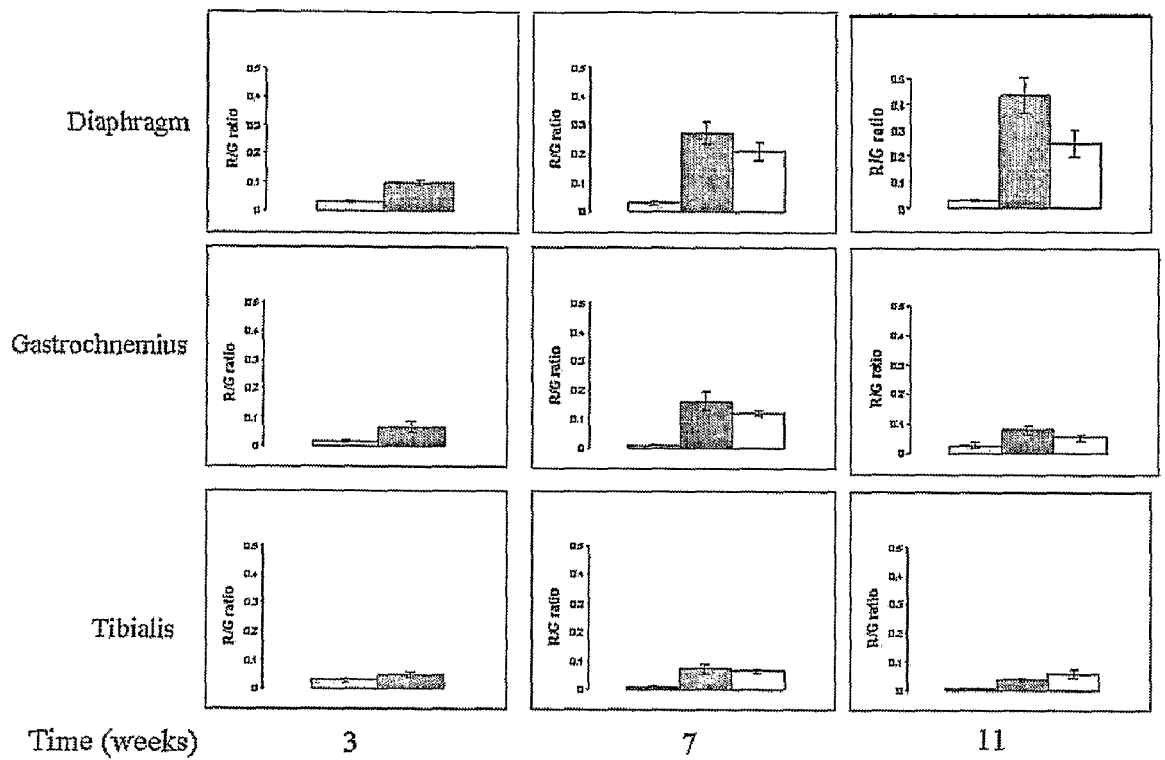
FIG. 3 is a bar chart demonstrating the effect of halofuginone on muscle fibrosis using staining and quantification by Image analysis.

FIG. 3 demonstrates that in the wild-type mice, the level of collagen was low in diaphragm, gastrochnemius and tibialis whereas in the mdx mice, an increase in the collagen content was observed in all muscles. The main increase was observed in the diaphragm; this was already evident at 3 weeks of age and reached 9 and 15-fold increase compared to the wild type at 7 and 11 weeks, respectively. In the gastrochnemius, an increase in the collagen content was observed already at 3 weeks of age with further increase at 7 weeks. At older ages, a decline in the collagen content was observed although the level was still higher than that in the wild type. Only a minute increase in collagen was observed in the tibialis. In the diaphragm, halofuginone reduced the collagen levels by 25% at 7 weeks (4 weeks of treatment) and by 53% at 11 weeks (8 weeks of treatment). In the gastrochnemius, halofuginone reduced the collagen content by 25% and 33% at 7 and 11 weeks, respectively. No effect of halofuginone on the collagen content was observed in the tibialis muscle.

Figure 4:
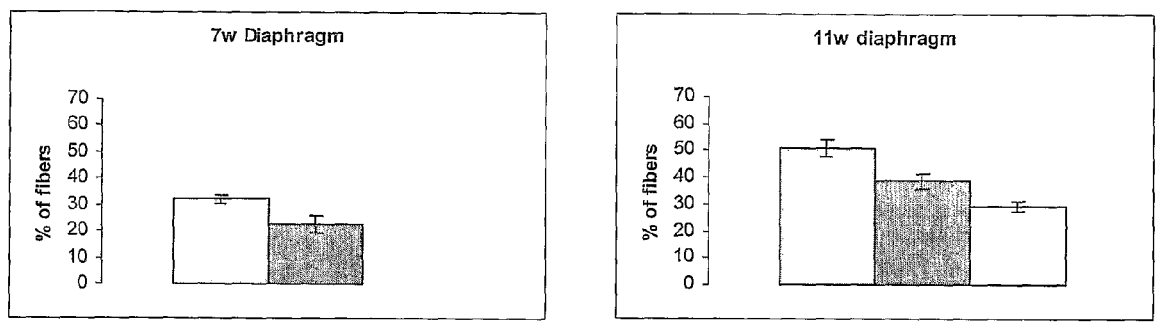
FIG. 4 is a bar chart illustrating muscle regeneration after halofuginone treatment.

FIG. 4 shows the effect of halofuginone 5 μg (purple) or 7.5 μg (off white) on muscle regeneration, with untreated mdx mice (blue) as control. In the wild type mice, the nucleus of each muscle fiber is located at the periphery of the cell. In the mdx mice small immature centrally nucleated fibers are observed, reflecting muscle regeneration from myoblasts that results in a balance between necrotic and regenerative processes in the early phase of the disease. After halofuginone treatment a major reduction in the number of diaphragm central nuclei was observed that was dose-dependent. These results suggest that halofuginone improved the muscle physiology and reduced the pressure on the mdx mice muscle to regenerate.

Discussion

In different muscular dystrophies and dystrophic syndromes, different muscle types are affected by fibrosis to a different extent. In the mdx mouse, which serves as a model for Duchenne muscle dystrophy (DMD), the most affected muscle is the diaphragm although other muscles are also affected. Consequently, the greatest effect of halofuginone in mdx mice was shown with regard to fibrotic diaphragm muscles, resulting in 53% inhibition of fibrosis and of the fibrotic process.

Together, the above results suggest that halofuginone is a potent inhibitor of muscle fibrosis in mdx mice by inhibiting collagen type I synthesis and may inhibit the need for muscle degeneration by inhibiting the myostatin pathway.

The above results further show that the extent of inhibition of fibrosis by halofuginone is dependent upon the extent of fibrosis. Halofuginone has been shown to inhibit fibrosis by inhibition of collagen synthesis in every muscle that is affected by fibrosis, but in muscles in which only minute increases in collagen synthesis occur, the inhibition of collagen synthesis caused by halofuginone may not be clearly demonstrable in the context of the experiment, for example during the time period tested.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. A method for reducing the progression of skeletal muscle fibrosis in a subject having muscular dystrophy, the method comprising administering to the said subject a pharmaceutically effective amount of halofuginone or a pharmaceutically acceptable salts of halofuginone in combination with a pharmaceutically acceptable carrier.

2. The method according to claim 1, wherein said muscular dystrophy is selected from the group consisting of Duchenne muscular dystrophy, Becker muscular dystrophy, Emery-Dreifuss Muscular Dystrophy, Limb-Girdle Muscular Dystrophy, Facioscapulohumeral Muscular Dystrophy, Myotonic Dystrophy, Oculopharyngeal Muscular Dystrophy, Distal Muscular Dystrophy, and congenital muscular dystrophy.

3. A method for improving or inducing skeletal muscle regeneration in a subject having muscular dystrophy, the method comprising administering to the said subject a pharmaceutically effective amount of halofuginone or a pharmaceutically acceptable salts of halofuginone in combination with a pharmaceutically acceptable carrier.

4. The method according to claim 3, wherein said muscular dystrophy is selected from the group consisting of Duchenne muscular dystrophy, Becker muscular dystrophy, Emery-Dreifuss Muscular Dystrophy, Limb-Girdle Muscular Dystrophy, Facioscapulohumeral Muscular Dystrophy, Myotonic Dystrophy, Oculopharyngeal Muscular Dystrophy, Distal Muscular Dystrophy, and congenital muscular dystrophy.

5. The method according to claim 3, wherein the improving of skeletal muscle regeneration occurs through inhibiting the TGFβ pathway and/or by inhibiting the Myostatin Smad3-dependent pathway.

* * * * *